United States Patent
Surenthiran (10) Patent No.: US 9,668,930 B2
(45) Date of Patent: Jun. 6, 2017

(54) THERAPEUTIC DEVICE (76) Inventor: Sangaralingam Shanmuga Surenthiran, Longfield (GB)

( * ) Notice: Subject to any disclaimer, the term of this patent is extended or adjusted under 35 U.S.C. 154(b) by 0 days.

(21) Appl. No.: 13/384,614

(22) PCT Filed: Jul. 20, 2010

(86) PCT No.: PCT/GB2010/001372
§ 371 (c)(1),
(2), (4) Date: Jan. 18, 2012

(87) PCT Pub. No.: WO2011/010087
PCT Pub. Date: Jan. 27, 2011

(65) Prior Publication Data
US 2012/0123191 A1    May 17, 2012

(30) Foreign Application Priority Data

Jul. 20, 2009 (GB) .................................. 0912579.0
Aug. 4, 2009 (GB) .................................. 0913577.3

(51) Int. Cl.
*A61H 5/00* (2006.01)
*A61M 21/00* (2006.01)

(52) U.S. Cl.
CPC ............... *A61H 5/00* (2013.01); *A61M 21/00* (2013.01); *A61M 2021/005* (2013.01);
(Continued)

(58) Field of Classification Search
CPC ..... A61H 5/00; A61M 21/00; A61M 2205/50; A61M 2021/0044; A61M 2021/005;
(Continued)

(56) References Cited

U.S. PATENT DOCUMENTS 5,343,261 A    8/1994  Wilson
5,619,291 A *  4/1997  Putnam ........................ 351/240
(Continued)

FOREIGN PATENT DOCUMENTS

DE    19905145    8/2000
WO     9600532    1/1996
WO    03088827   10/2003

OTHER PUBLICATIONS

Goldberg, Charlie M.D. A practical guide to clinical medicine. USCSD School of Medicine, "http://:web.archive.org/web/20080312232409/http://meded.ucsd.edu/clinicalmed/eye.htm", Sep. 12, 2008.*

(Continued)

*Primary Examiner* — Christine H Matthews
*Assistant Examiner* — Kaylee Wilson
(74) *Attorney, Agent, or Firm* — Fogg & Powers LLC (57) ABSTRACT A therapeutic device comprising a first visual signaling element, a second visual signaling element positioned separately from the first visual signaling element, and a third visual signaling element positioned between the first and second visual signaling elements. A control apparatus controls the first, second and third signaling elements, and is arranged to alternately activate the first and second visual signaling elements for a first period of time, and to activate the third visual signaling element for a second period of time subsequent to the first period of time.

12 Claims, 6 Drawing Sheets

(52) U.S. Cl.
CPC ............ *A61M 2021/0027* (2013.01); *A61M 2021/0044* (2013.01); *A61M 2205/50* (2013.01); *A61M 2230/62* (2013.01); *A61M 2230/63* (2013.01)

(58) Field of Classification Search
CPC ...... A61M 2021/0027; A61M 2230/62; A61M 2230/63
USPC ..................................... 600/26, 27; 351/203
See application file for complete search history.

(56) References Cited

U.S. PATENT DOCUMENTS

| | | | |
|---|---|---|---|
| 5,833,466 A | | 11/1998 | Borg |
| 5,953,102 A | * | 9/1999 | Berry ............................ 351/247 |
| 6,056,403 A | | 5/2000 | Fisher et al. |
| 6,742,892 B2 | * | 6/2004 | Liberman .................... 351/203 |
| 2004/0075811 A1 | * | 4/2004 | Liberman .................... 351/203 |
| 2007/0015127 A1 | | 1/2007 | Teyf |
| 2008/0073201 A1 | * | 3/2008 | Van Gysel et al. ............. 203/34 |
| 2008/0278682 A1 | * | 11/2008 | Huxlin et al. ................ 351/203 |
| 2009/0082685 A1 | | 3/2009 | Stabler et al. |
| 2009/0290123 A1 | * | 11/2009 | Yang ............................ 351/203 |

OTHER PUBLICATIONS

NeuroInnovations. "Alcohol aversion via EMDR software from Neuro Innovations". [Video File]. Jun. 2, 2009. Retrieved from https://youtu.be/kLIS2oCNzsg?list=PL7F78128256292AFF.*

EMDR PRO "EMDR software from Neuro Innovations developers of EMDR Pro", http://www.neuroinnovations.com/emdr_software.html. Accessed online on Feb. 3, 2016.*

International Searching Authority, "International Search Report", Mailed Jan. 27, 2011, Published in: WO.

"Technology in Support of the EMDR Clinician", "www.neurotekcorp.com accessed Mar. 7, 2009"p. 1 Publisher: Neurotek Corporation.

Bisson et al, "The Management of PTSD in Adults and Children in Primary and Secondary Care", "Post-traumatic Stress Disorder", 2005, pp. 1-176, Publisher: National Collaborating Centre for Mental Health.

Shapiro, "Eye Movement Desensitization: A New Treatment for Post-Traumatic Stress Disorder", "Journal of Behavior therapy and Experimental Psychiatry", 1989, pp. 211-217, vol. 20, No. 3.

* cited by examiner

THERAPEUTIC DEVICE

This application claims priority to International Patent Application No. PCT/GB2010/001372 filed on Jul. 20, 2010 which claims priority to Great Britain Application No. 0912579.0 filed on Jul. 20, 2009 and Great Britain Application No. 0913577.3 filed on Aug. 4, 2009.

BACKGROUND OF THE INVENTION

The present invention concerns methods of therapy, and therapeutic devices associated with those methods.

Eye Movement Desensitization and Reprocessing (EMDR) is a well-known method of therapy used for example in the treatment of individuals with post-traumatic stress disorder (PTSD). (See for example Shapiro, F. (1989), Eye movement desensitisation: a new treatment for post-traumatic stress disorder, Journal of Behavior Therapy and Experimental Psychiatry, 20, 211-217.) EMDR therapy is used to desensitise an individual to a past traumatic experience, to prevent or reduce any adverse symptoms associated with the memory of the experience. EMDR therapy has been approved by the United Kingdom National Institute for Health and Clinical Excellence (NICE) for use in the treatment of PTSD (see http://www.nice.org.uk/nicemedia/pdf/CG026fullguideline.pdf)

EMDR therapy comprises a number of phases. For example, the therapy may begin with an initial phase in which a patient's history is taken, the therapist identifies potential targets for EMDR, and an overall treatment plan is devised. Following this there are phases in which the EMDR treatment itself is performed. In later phases the results of the treatment are assessed, any further treatment is performed if necessary, and finally the patient is debriefed and given any appropriate information and support.

A key aspect of EMDR treatment is that, during a desensitisation phase, the patient undergoing therapy is instructed to move their eyes in a particular way while mentally focusing on an image associated with the traumatic experience. It is believed that the particular eye movement helps the patient to mentally process the memory of the traumatic experience, desensitising them to the memory and thus preventing or reducing any associated symptoms.

The particular eye movement required is a side-to-side tracking movement. This type of eye movement is usually called "pursuit eye movement", and contrasts with "saccadic eye movement" in which the eye moves from one position to another in a single extremely quick movement.

The eye movement is often facilitated by instructing the patient to track with their eyes an object that is moved from side to side by the therapist. (The object may simply be the therapist's finger, for example.)

Alternatively, devices to facilitate the side-to-side tracking movement of the eyes are also known.

WO 96/00532 A1 (Wilson) describes a device which has a number of light-emitting diodes (LEDs) mounted along a bar which is positioned horizontally in a patient's field of vision. The device is arranged so that the light-emitting diodes are lit up in sequence from one end of the bar to the other and back again, with the sequence being repeated. Consequently, when a patient is instructed to focus on the LEDs as they light up their eyes will as a result track from side to side.

The present invention concerns a new method of therapy similar to (but different from) EMDR. Amongst other things, the invention seeks to provide a therapeutic device based on that new method of therapy.

SUMMARY OF THE INVENTION

A first aspect of the present invention provides a therapeutic device comprising:
 a first visual signaling element;
 a second visual signaling element positioned separately from the first visual signaling element;
 a third visual signaling element positioned between the first and second visual signaling elements;
 a control apparatus for controlling the first, second and third signaling elements;
 wherein the control apparatus is arranged to:
 for a first period of time, to alternately activate the first and second visual signaling elements;
 for a second period of time subsequent the first period of time, to activate the third visual signaling element.

The device can be used when performing on a patient a new method of therapy (described below) involving eye movements. The device provides signals to the patient to tell them where to look during the therapy. The device can be used by a therapist to instruct the patient, enabling the therapist to more easily perform supplementary tasks while the therapy is being performed, such as providing verbal suggestions (e.g. hypnotic suggestions). Further, the device may also provide greater consistency in the therapy, for example in the positions where the patient is instructed to look and for what periods of time. The device may also be used by a patient on occasions after an initial therapy session with a therapist, to allow the patient to undergo further episodes of the therapy in which a therapist does not need to be present.

The therapeutic device may be a personal computer.

The first, second and third visual signaling elements may be regions of one or more visual display units. Each region of the one or more visual display units may be activated by displaying an image at a position within the region. Alternatively the image may fill the entirety of the region. On each occasion a region is activated, the image may be displaying in a different position within the region. The position of the image may be determined according to a pattern, or alternatively the image may be positioned at random within the region.

The visual display unit or units may be liquid-crystal displays.

Alternatively, the first, second and third visual signaling elements may be distinct light sources. The light sources may be light-emitting diodes.

Preferably, during the first period of time the first and second signaling elements are alternately activated for a period of between 0.1 and 2 seconds. More preferably, the first and second signaling elements are alternately activated for a period of between 0.5 and 1 seconds.

Preferably, the first period of time is between 10 and 30 seconds. More preferably, the first period of time is between 15 and 20 seconds.

Advantageously, the device further comprises one or more audio signaling elements, and the control apparatus is arranged to activate the one or more audio signaling elements to provide an audio signal on activation of the first and second visual signaling elements. The audio signaling elements may be audio speakers or headphones.

A second aspect of the present invention provides a method performed on a computer device comprising a visual display, the visual display comprising a first region, and second region positioned separately from the first region, and a third region positioned between the first and second regions, comprising the steps of:

for a first period of time, alternately activating the first and second regions of the visual display;

for a second period of time following the first period of time, activating the third region of the visual display visual signaling element.

The first, second and third regions of the visual display may be distinct regions of a single visual display unit. Each region of the visual display may be activated by displaying an image at a position within the region. On each occasion a region is activated, the image may be displayed in a different position within the region. The visual display unit or units may be liquid-crystal displays.

Preferably, during the first period of time the first and second portions of the visual display are alternately activated for a period of between 0.1 and 2 seconds. More preferably, the first and second portions of the visual display are alternately activated for a period of between 0.5 and 1 seconds.

Preferably, the first period of time is between 10 and 30 seconds. More preferably, the first period of time is between 15 and 20 seconds.

Advantageously, the computer device further comprises an audio output, and the audio output is activated when the first and second portions of the visual display audio signal are activated. The audio output may be provided by audio speakers or headphones.

A third aspect of the present invention provides a computer program product arranged to perform, when executed on a computer device, the steps of any of the methods described above.

A fourth aspect of the present invention provides a method of performing therapy on a patient comprising the steps of:

for a first period of time, instructing the patient to look between a first position and a second position separate from the first position using a single saccadic eye movement;

for a second period of time following the first period of time, instructing the patient to look at a third position between the first and second positions and to move the focus of their eyes towards themselves from the third position towards a point between their eyes.

This novel method of therapy has been used to treat patient with a variety of problems, with apparent success. It is believed that the treatment may work by directly accessing the primitive areas of the cerebral cortex and limbic system.

The patient may be instructed to move the focus of their eyes from the third position towards the point between their eyes using a tracking (pursuit) eye movement. Alternatively, the patient may be instructed to move the focus of their eyes using a single saccadic eye movement.

In the first period of time the patient may be instructed to look at the first and second positions by means of the therapist performing the therapy signaling with fingers held in the first and second positions respectively. Similarly, in the second period of time the patient may be instructed to look at the third position and to move the focus of their eyes towards themselves by means of the therapist moving a finger from the third position towards the patient.

Preferably, during the first period of time the patient is instructed to look at first and second positions for a period of between 0.1 and 2 seconds. More preferably, during the first period of time the patient is instructed to look at first and second positions for a period of between 0.5 and 1 seconds.

Preferably, the first period of time is between 10 and 30 seconds. More preferably, the first period of time is between 15 and 20 seconds.

Preferably, the second period of time is between 0.5 and 2 seconds.

It will of course be appreciated that features described in relation to one aspect of the present invention may be incorporated into other aspects of the present invention. For example, the method of the invention may incorporate any of the features described with reference to the apparatus of the invention and vice versa.

DESCRIPTION OF THE DRAWINGS

Embodiments of the present invention are now described by way of example only with reference to the accompanying schematic drawings of which.

DETAILED DESCRIPTION

The method of therapy in accordance with an embodiment of the invention is now described. As with EMDR therapy, the therapy comprises a number of phases, for example initial phases in which the patient is assessed, and later phases in which the results of the treatment are assessed, any further treatment is performed if necessary.

Figure 1:
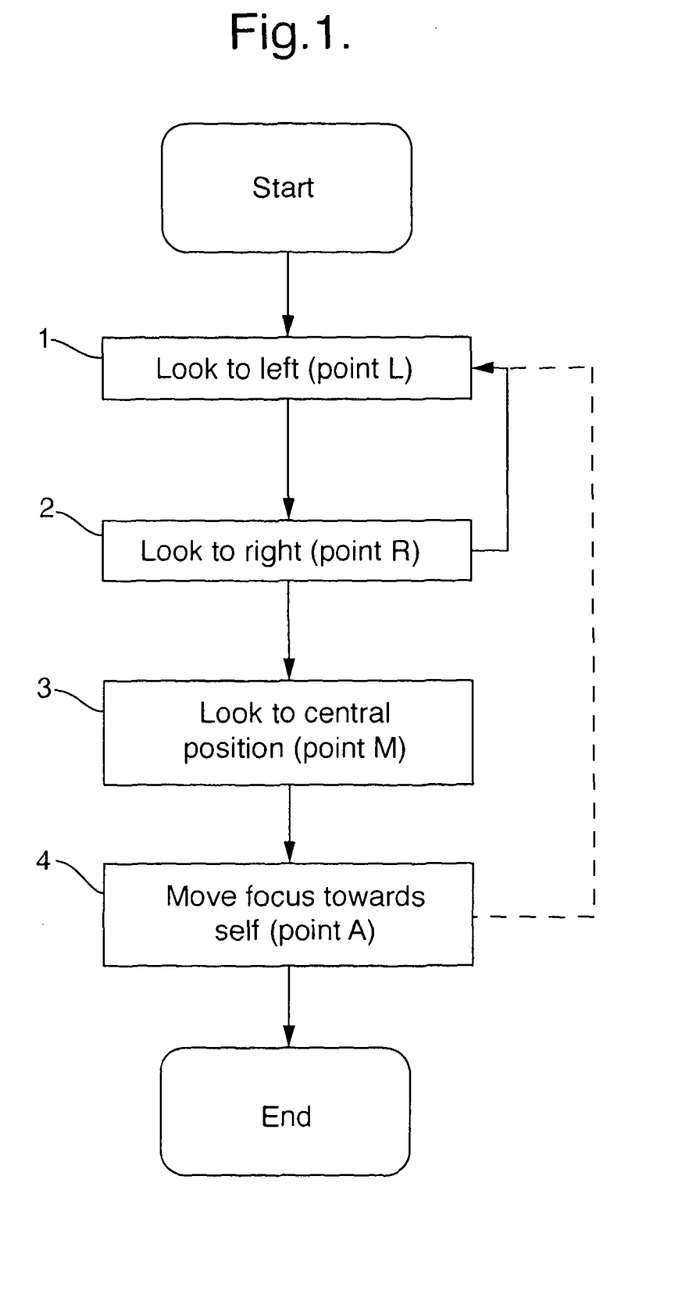
FIG. 1 is a flow chart showing a method of therapy according to an embodiment of the invention.
Figure 2:
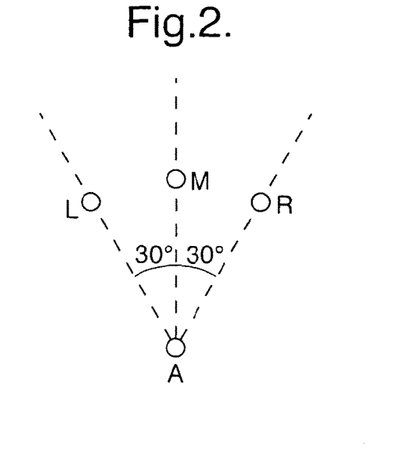
FIG. 2 is a schematic diagram showing the positions of elements relating to the method of therapy of FIG. 1.

A key aspect of the treatment is shown in the flow chart of FIG. 1 and schematic diagram of FIG. 2. As with EMDR, the patient undergoing therapy is instructed to move their eyes in a particular way. However, the particular way in which the patient is instructed to move their eyes is very different to the eye movement used in EMDR.

As shown in FIG. 2, a patient is positioned at point A, facing towards point M. In front of the patient is a point L, which is on a line roughly 30° to the left of the point M, and a point R, which is on a line roughly 30° to the right of the point M.

In a first step, the patient is instructed to look at point L (step 1 of FIG. 1). After a period of roughly half a second, the patient is instructed to look at the point R (step 2). Notably, the patient is instructed to move their focus directly from the point L to point R, using a single saccadic eye movement, without focusing on any points in between the points L and R.

Again after a period of roughly half a second, the patient is instructed to look at point L (step 1 again). Similarly, the patient is instructed to move their focus directly from the point R to point L using a single saccadic eye movement, without focusing on any points in between the points L and R.

The above steps are repeated a number of times, for example 30 times for each step over a period of around 30 seconds. Following that, the patient is instructed to look at the point M directly in front of them (step 3), and then immediately to move their focus from the point M towards themselves along the line between points M and A over a period of roughly one second (step 4). As a result of this final step the patient becomes cross-eyed.

The entire set of steps 1 to 4 may be repeated, for example 2 or 3 times.

In order to facilitate the eye movements of the patient, the therapist may for example use their fingers to signal where the patient should be focusing. For example, during the first stage of the process (steps 1 and 2 of FIG. 1), the therapists holds their right and left hands at points L and R respectively. To instruct the patient to look at point L (step 1), the therapist signals with their right hand, for example by crooking their left index finger. Similarly, to instruct the patient to look at point R (step 2) the therapist signals with their left hand, again for example by crooking their right index finger.

Once the patient has looked at points L and R the required number of times, the therapist moves their finger to point M to signal the patient to look at that point (step 3), and then immediately moves their finger along the line between points M and A, towards the patient's nose. As the patient's focus follows the path of the therapist's finger along the line between points M and A, they will become cross-eyed as required.

The treatment has been used as described in the following experiments, with apparent success. It is believed that the treatment may work by directly accessing the primitive areas of the cerebral cortex and limbic system.

EXAMPLE 1

The patient had the condition of tinnitus (ringing sound in the ears). Following the treatment the patient experienced reduced levels of sound, and in particular found that their feelings of anxiety regarding the condition were greatly reduced.

EXAMPLE 2

The patient had one side of their body paralysed following a cerebral artery stroke. As a result of this, the patient had developed an aversion to open spaces. In addition, the patient had a short temper and suffered from bouts of "road rage". Following treatment for the aversion to open spaces, the aversion was reduced. It was also found that the short temper of the patient was reduced following the treatment, even though the treatment was not directly aimed at treating this problem.

EXAMPLE 3

The patient experienced chronic neck problems including neck pain. Following treatment the neck pain was much reduced for a short period of time.

A therapeutic device in accordance with an embodiment of the invention is now described. The therapeutic device may be used by a therapist to facilitate the required eye movement of the patient. Alternatively, the therapeutic device may be used by a patient at a later date, for example in their own home, to "reinforce" the treatment.

Figure 3A:
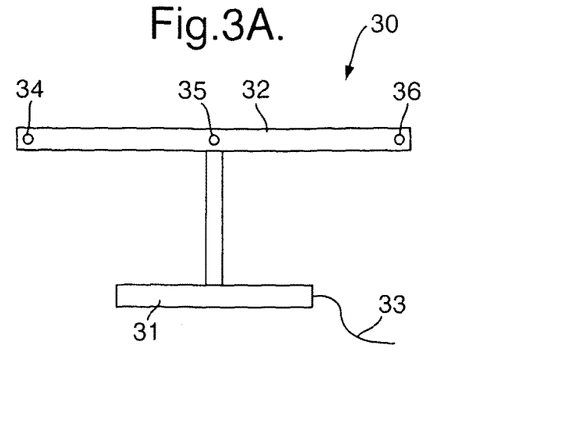
FIG. 3A is a schematic diagram of a therapeutic device according to a further embodiment of the invention.

A schematic diagram of the therapeutic device is shown in FIG. 3A. The therapeutic device 30 comprises a stand 31, which can be used to stand the therapeutic device 30 on a table, for example. The stand includes a control apparatus 37 for the therapeutic device (see FIG. 3B), which can be connected to a power supply (not shown) by means of a cable 33.

A horizontal bar 32 is mounted on the stand 31. A first light-emitting diode (LED) 34 is mounted at the left-hand end of the horizontal bar 32. A second LED 36 is mounted at the right-hand end of the horizontal bar 32. Finally, a LED 35 is mounted at the right-hand end of the horizontal bar 32.

Figure 3B:
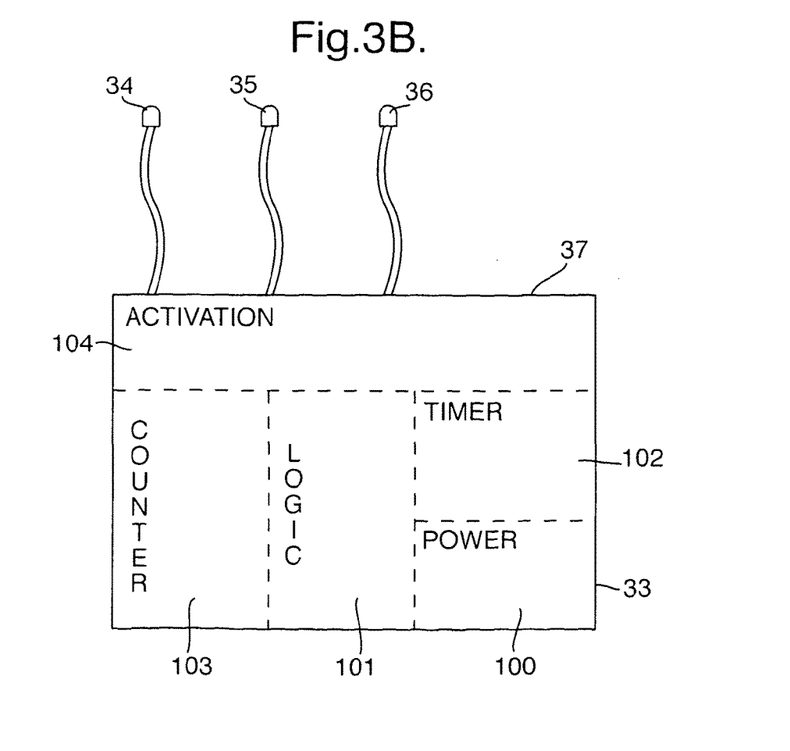
FIG. 3B is a schematic diagram of the control circuit of the therapeutic device of FIG. 3A.

The control apparatus 37 of the therapeutic device 30 is shown in more detail in FIG. 3B. The control apparatus 37 comprises a power circuit 100 connected to the power supply by the cable 33, which converts the power provided by the power supply into a supply for use by rest of the control apparatus 37. A logic circuit 101 provides general operation of the control apparatus 37. The logic circuit 101 has available for its use a timer circuit 102, a counter circuit 103, and an activation circuit 104, amongst other things. The timer circuit 102 and counter circuit 103 are used to time and count steps in the operation of the therapeutic device 30 as described in detail below. The activation circuit 104 is connected to and operates the LEDs 34, 35 and 36.

In use, the therapeutic device 30 is positioned in front of the patient, for example on a table before which the patient sits. The therapeutic device 30 is positioned so that the third LED 35 is directly in front of the patient, the first LED 34 is on a line roughly 30° to the left of the third LED 35, and the second LED 36 is on a line roughly 30° to the right of the third LED 35. Thus, relative to the patient, the first LED 34, second LED 36 and third LED 35 are in the equivalent of the positions L, M and R of FIG. 2 respectively.

Figure 4:
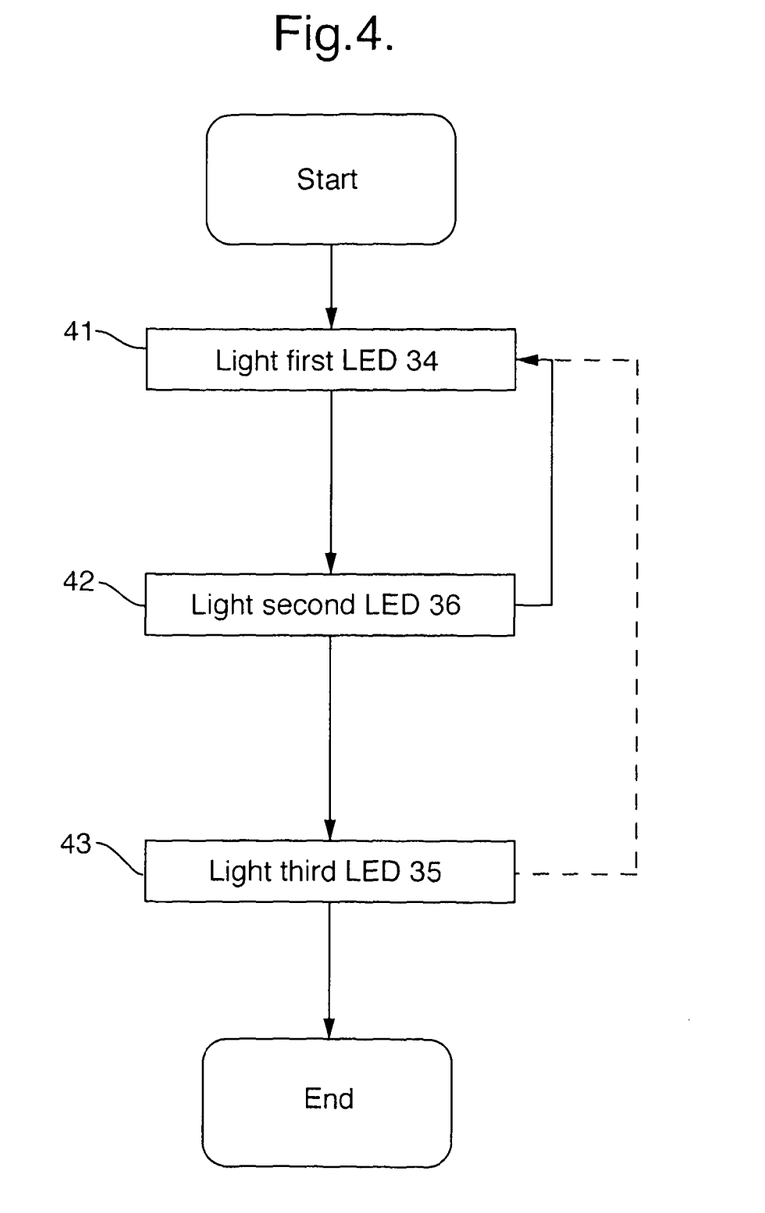
FIG. 4 is a flow chart showing the operation of the therapeutic device of FIG. 3A.

When activated, the therapeutic device 30 is operated by the logic circuit 101 of the control apparatus 37 as shown in FIG. 4. First, the first LED 34 is lit by the activation circuit 104 for a period of roughly half a second (step 41), determined by the timer circuit 102. The second LED 36 is then lit by the activation circuit 104 for a period of roughly half a second (step 42), again determined by the timer circuit 102. These two steps are repeated a number of times, with the number of steps being counted by the counter circuit 103. When a pre-determined number of steps have occurred, the third LED 35 is lit by the activation circuit 104. In each case the lighting of an LED is intended to signal the patient to move their eyes so as to focus upon that LED, and thus the therapeutic device 30 in operation facilitates the eye movements required of the patient.

The entire set of steps 41 to 43 may be repeated, for example 2 or 3 times.

A therapeutic device in accordance with a further embodiment of the invention is now described. As before, the therapeutic device may be used by a therapist to facilitate the required eye movement of the patient, or may be used by a patient at a later date to "reinforce" the treatment.

Figure 5:
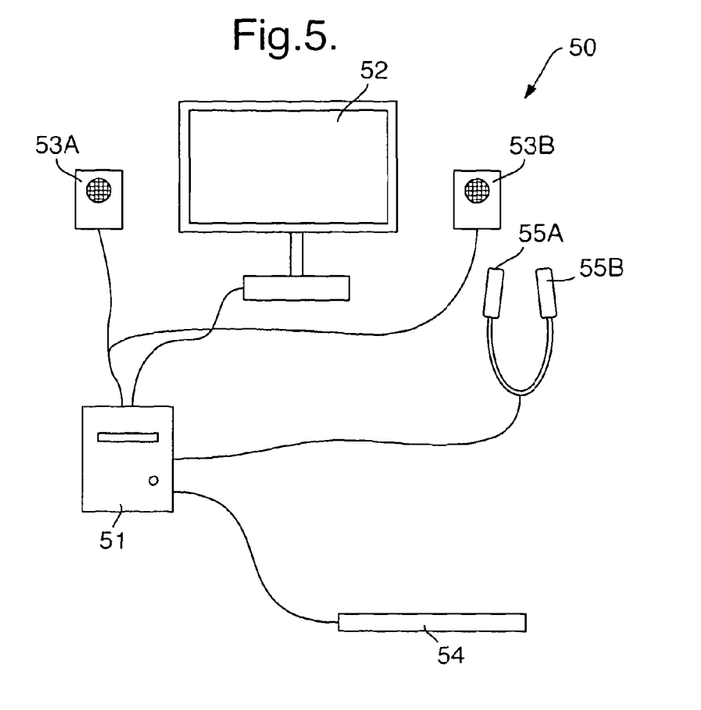
FIG. 5 is a schematic diagram of a therapeutic device according to a further embodiment of the invention.

A schematic diagram of the therapeutic device is shown in FIG. 5. The therapeutic device 50 comprises a personal computer (PC) 51. The computer has a liquid-crystal display (LCD) screen 52, which may be positioned on a table or, for example, mounted upon a wall.

In use, the therapeutic device 50 works similarly to that of the previously described embodiment. The LCD screen 52 of the therapeutic device 50 is positioned in front of the patient, for example on a table before which the patient sits, or on a wall at eye height in front of the patient. The LCD screen 52 is positioned so that the central portion of the LCD screen 52 is directly in front of the patient, a left-hand portion of the LCD screen 52 is on a line roughly 30° to the left of the central portion of the LCD screen 52, and a right-hand portion of the LCD screen 52 is on a line roughly 30° to the right of the central portion of the LCD screen 52. Thus, similarly to the previous device, relative to the patient, the left-hand portion of the LCD screen 52, right-hand portion of the LCD screen 52 and central portion of the LCD screen 52 are in the equivalent of the positions L, M and R of FIG. 2 respectively.

Figure 6A:
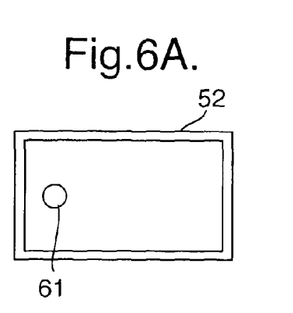
FIGS. 6A to 6C are schematic diagrams showing possible display configurations of the therapeutic device of FIG. 5.
Figure 6B:
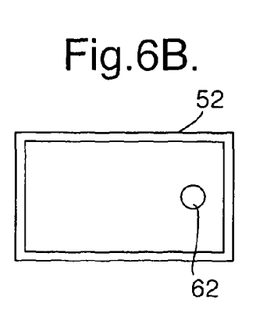
Figure 6C:
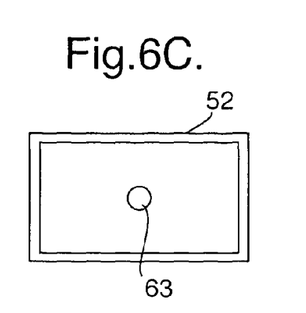
Figure 7:
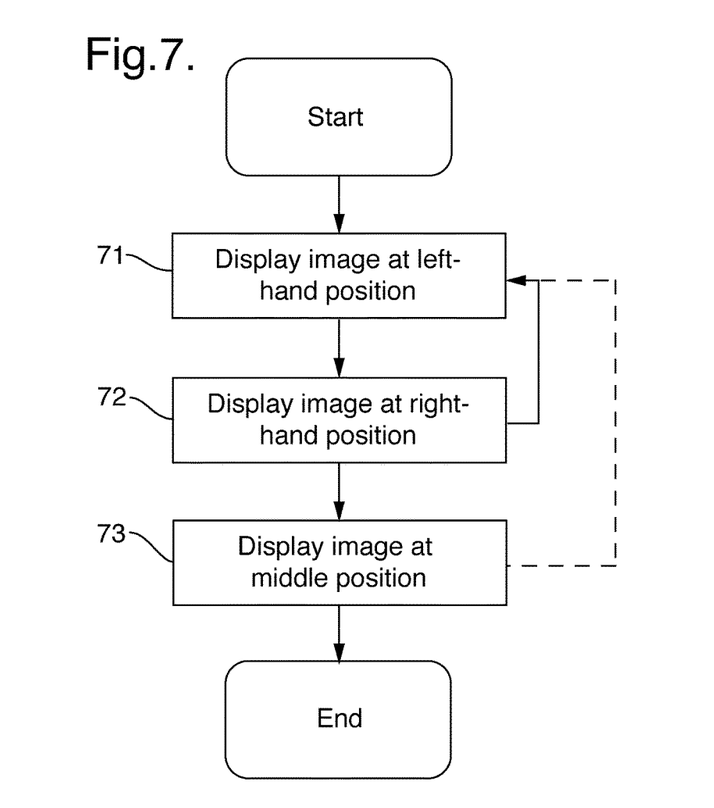
FIG. 7 is a flow chart showing the operation of the therapeutic device of FIG. 5.

When activated, the therapeutic device 50 works as shown in FIG. 7. First, an image is displayed the left-hand portion of the LCD screen 52 for roughly half a second (step 71). (See the circle 61 of FIG. 6A.) An image is displayed the right-hand portion of the LCD screen 52, again for roughly half a second (step 72). (See the circle 62 of FIG. 6B.) These two steps are repeated a number of times, following which an image is displayed the central portion of the LCD screen 52. (See the circle 63 of FIG. 6C.) In each case the image is intended to signal the patient to move their eyes so as to focus upon that image, and thus the therapeutic device 50 in operation facilitates the eye movements required of the patient.

The entire set of steps 71 to 73 may be repeated, for example 2 or 3 times.

While FIGS. 6A to 6C show the image as a circle, any image suitable to act as a signal for the patient can be used. For example, points of light, letters, numbers, symbols, words, drawings or photographs could be used. The letters, numbers, symbols and words could be displayed in varying sizes, typefaces and colours. Words, symbols, drawings or photographs that are of relevance to the issues which are intended to be treated by the therapy could be selected by the therapist. A single image could be used for an entire cycle of treatment, or a variety of images could be used.

Figure 8:
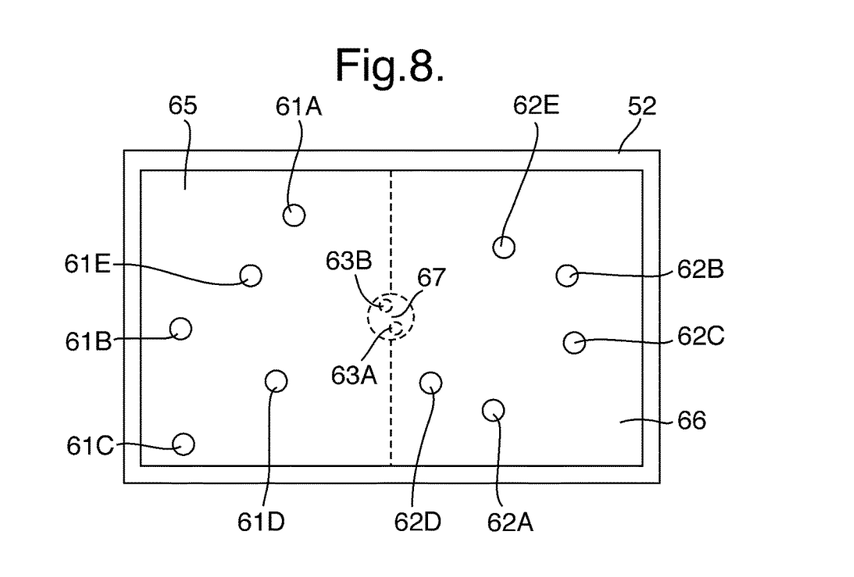
FIG. 8 is a schematic diagram showing possible display configurations of the therapeutic device of FIG. 5.

Referring to FIG. 8, the left-hand portion of the LCD screen 52 in which the image is displayed may comprise a region 65 covering the majority of the left-hand side of the LCD screen. The circle (or other image) may be displayed in a different position within region 65 in different occurrences of the step 71; for example, circles 61A to 61E may be displayed in successive steps. The position of the circles 61A to 61E may be random, or may follow a pattern.

Similarly, the right-hand portion of the LCD screen 52 in which the image is displayed may comprise a region 66 covering the majority of the right-hand side of the LCD screen, and circles (or other images) 62A to 62E may be displayed in different positions within region 66 in different occurrences of the step 72. Finally, the central portion of the LCD screen 52 may comprise a region 67, and the circle (or other image) may be displayed in a number of different positions within the region 67 during step 73, for example at position 63A or position 63B.

Figure 9A:
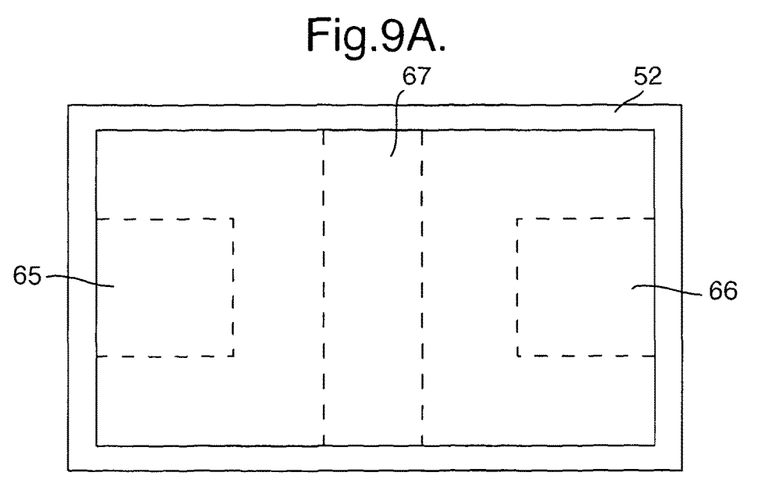
FIG. 9A is a schematic diagram showing possible display configurations of the therapeutic device of FIG. 5.
Figure 9B:
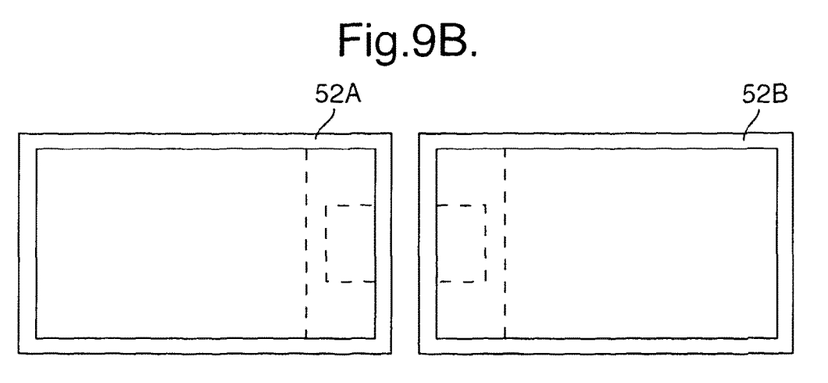
FIG. 9B is a schematic diagram showing possible display configurations of the therapeutic device of a further embodiment of the invention.

It will be appreciated that other suitable regions of the LCD screen 52 can be used for the left-hand, right-hand and central portions. For example, as shown in FIG. 9A, the left-hand and right-hand portions of the LCD screen 52 could be square regions 65 and 66 respectively, with the central portion being a rectangular region 67 in the middle of the LCD screen 52. In a further related embodiment, the therapeutic device 50 may comprise a PC 51 with two adjacent LCD screens 52A and 52B, as shown in FIG. 9B. The left-hand and right-hand portions could then be rectangular regions 65 and 66 respectively, with the central portion being a rectangular region 67 which crosses the boundary between the LCD screens 52A and 52B.

Returning to FIG. 5, the therapeutic device 50 comprises further supplementary elements that can be used during treatment, as described below.

The therapeutic device 50 comprises speakers 53A and 53B connected to the PC 51. The speakers may for example be free-standing, mounted on the LCD screen 52, or alternatively headphones could be used by the patient. The speakers 53A and 53B make a sound (such as a click) each time an image is displayed. Alternatively, a different sound may be made by the speakers; for example, a word or words may be spoken. The words may be selected by the therapist to be of relevance to the issues which are intended to be treated by the therapy. Both speakers may make a sound each time an image is displayed, or the left-hand speaker 53A may make a sound when an image is displayed on the left-hand side of the LCD screen 52 (and similarly for the right-hand speaker 53B and right-hand side of the LCD screen 52), for example.

The therapeutic device also comprises elements that are able to provide feedback from the patient during treatment. The feedback can be used to provide information to the therapist about the treatment as the treatment is in progress, or the information may be recorded to be analysed at a later date. The feedback may alternatively (or in addition) be used to dynamically alter the treatment itself. A pressure sensing device 54 comprising a firm foam pad incorporating a pressure sensor is connected to the PC 51. During treatment, the patient stands on the pressure sensing device 54, which provides information about any changes in the patient's centre of gravity during the treatment. Further, hand-held pressure sensing devices 55A and 55B comprising firm rubber cylinders each incorporating pressure sensors are connected to the PC 51. During treatment, the patient holds the hand-held pressure sensing devices 55A and 55B in each hand. The patient may be instructed to squeeze the pressure sensing devices 55A and 55B when each image is displayed, and they then provide information about any changes in the pressure applied by the patient during the treatment.

It will be appreciated that any of these described supplementary elements could be used with a therapeutic device according to other embodiments of the present invention, for example with the therapeutic device 30 of the first embodiment.

It will further be appreciated that the therapeutic device 50 could be provided by means of computer software running upon a standard personal computer. The computer software could be provided for example by means of a computer program product such as a CD or DVD on which the software is stored, a program downloaded and installed upon the computer, or a program operating remotely such as over the Internet.

Whilst the present invention has been described and illustrated with reference to particular embodiments, it will be appreciated by those of ordinary skill in the art that the invention lends itself to many different variations not specifically illustrated herein. By way of example only, certain possible variations will now be described.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A device for use by a therapist to treat one or more mental issues comprising:
   a first visual signaling element;
   a second visual signaling element positioned separately from the first visual signaling element;
   a third visual signaling element positioned between the first and second visual signaling elements;
      wherein the first, second and third visual signaling elements are regions of one or more visual display units;
      wherein each region of the one or more visual display units is activated when an image is displayed at a position within the region and inactive when no image is displayed within the region, wherein the images displayed are words, drawings, or photographs, selected by the therapist that are of relevance to the one or more mental issues which are intended to be treated;
   a control apparatus for controlling the first, second and third signaling elements;
   wherein the control apparatus is configured to:
      for a first period of time, consecutively and alternately activate the first and second visual signaling elements, wherein the third visual signaling element is inactive during the first period of time; and
      for a second period of time subsequent the first period of time, activate the third visual signaling element.

2. The device as claimed in claim 1, wherein the device is a personal computer.

3. The device as claimed in claim 1, wherein on each occasion a region is activated, the image is displayed at a different position within the region.

4. The device as claimed in claim 1, wherein the one or more visual display units are liquid-crystal displays.

5. The device as claimed in claim 1, wherein during the first period of time the first and second signaling elements are alternately activated for a period of between 0.1 and 2 seconds.

6. The device as claimed in claim 1, wherein the first period of time is between 10 and 30 seconds.

7. A method performed by a computer device comprising a visual display, wherein the computer device is for use by a therapist to treat one or more mental issues, the visual display comprising a first region, and a second region positioned separately from the first region, and a third region positioned between the first and second regions, wherein the first, second and third regions of the visual display are distinct regions of a single visual display unit and wherein each region of the visual display is activated when an image is displayed at a position within the region and inactive when no image is displayed within the region, wherein the images displayed are words, drawings, or photographs, selected by the therapist that are of relevance to the one or more mental issues which are intended to be treated, comprising the steps of:
   for a first period of time, consecutively and alternately activating the first and second regions of the visual display, wherein the third region of the visual display is inactive during the first period of time;
   for a second period of time following the first period of time, activating the third region of the visual display.

8. The method as claimed in claim 7, wherein on each occasion a region is activated, the image is displayed at a different position within the region.

9. The method as claimed in claim 7, wherein the visual display is one or more liquid-crystal displays.

10. The method as claimed in claim 7, wherein during the first period of time the first and second regions of the visual display are alternately activated for a period of between 0.1 and 2 seconds.

11. The method as claimed in claim 7, wherein the first period of time is between 10 and 30 seconds.

12. A program product comprising non-transitory processor-readable storage medium on which program instructions are embodied, wherein the program instructions are configured, when executed by at least one programmable processor, to cause the at least one programmable processor to perform the steps of the method of claim 7.

* * * * *